US010058678B2

(12) United States Patent
Schaffner

(10) Patent No.: US 10,058,678 B2
(45) Date of Patent: Aug. 28, 2018

(54) CATHETER ASSEMBLIES HAVING A PROTECTIVE SHEATH AND METHODS OF MANUFACTURE

(71) Applicants:ACOTEC SCIENTIFIC CO. LTD, Beijing (CN); Silvio Schaffner, Berlingen (CH)

(72) Inventor: Silvio Schaffner, Berlingen (CH)

(73) Assignees: ACOTEC SCIENTIFIC CO. LTD, Beijing (CN); SCHAFFNER SILVIO, Berlingen (CH)

( * ) Notice: Subject to any disclaimer, the term of this patent is extended or adjusted under 35 U.S.C. 154(b) by 0 days.

(21) Appl. No.: 14/363,815

(22) PCT Filed: Sep. 13, 2013

(86) PCT No.: PCT/IB2013/058522
§ 371 (c)(1),
(2) Date: Jun. 9, 2014

(87) PCT Pub. No.: WO2014/049482
PCT Pub. Date: Apr. 3, 2014

(65) Prior Publication Data
US 2015/0190612 A1    Jul. 9, 2015

(30) Foreign Application Priority Data

Sep. 27, 2012  (IT) .............................. PD2012A0283

(51) Int. Cl.
*A61M 25/00* (2006.01)
*A61M 39/10* (2006.01)
*A61M 25/10* (2013.01)

(52) U.S. Cl.
CPC .... *A61M 25/0045* (2013.01); *A61M 25/0014* (2013.01); *A61M 25/0054* (2013.01);
(Continued)

(58) Field of Classification Search
CPC .......... A61M 25/0054; A61M 25/0013; A61M 25/1025; A61M 25/0026; A61M 25/0014; A61M 39/105; A61M 25/104
See application file for complete search history.

(56) References Cited

U.S. PATENT DOCUMENTS 7,662,144 B2 *   2/2010   Chan ................. A61M 25/0009
                                                604/264
2013/0150807 A1 *  6/2013  Hamuro ............ H01R 13/5841
                                                604/264

FOREIGN PATENT DOCUMENTS

EP    0616817 A1   9/1994
EP    0937480 A1   8/1999
(Continued)

*Primary Examiner* — Imani Hayman
(74) *Attorney, Agent, or Firm* — Robert E. Alderson, Jr.

(57) ABSTRACT

Catheters and methods of making catheters are provided which include a connector with a guide wire channel and an inflation channel, a shaft extending from a proximal end to a distal end and having a guide wire lumen and an inflation lumen, the shaft being connected, at its proximal end, to the connector so that said guidewire lumen and inflation lumen are mechanically and fluidly connected with said guide wire channel and inflation channel respectively. The connection is realized in correspondence to a kink portion. Such catheters may include a protective sheath placed around an external wall of the shaft extending from a first sheath end, axially placed at a first distance from the proximal end of the shaft so as to allow direct contact and fixation between the external wall of the shaft and the internal wall of the kink portion, to a second sheath end.

19 Claims, 2 Drawing Sheets

(52) U.S. Cl.
CPC ........... *A61M 39/10* (2013.01); *A61M 25/104* (2013.01); *A61M 25/1025* (2013.01)

(56) References Cited

FOREIGN PATENT DOCUMENTS

| EP | 1010439 A1 | 6/2000 |
| WO | 9419039 A1 | 9/1994 |
| WO | 0147592 A1 | 7/2001 |

\* cited by examiner

CATHETER ASSEMBLIES HAVING A PROTECTIVE SHEATH AND METHODS OF MANUFACTURE

CROSS-REFERENCE TO RELATED APPLICATIONS

This application is a National Phase Application of PCT International Application No. PCT/IB2013/058522, International Filing Date, Sep. 13, 2013, claiming priority to Italian Patent Application No. PD2012A000283, filed Sep. 27, 2012, each of which is hereby incorporated by reference in its entirety.

FIELD OF THE INVENTION

The present invention relates to a catheter assembly, in particular for percutaneous transluminal angioplasty (PTA) balloon catheters with coaxial or dual-lumen construction.

BACKGROUND OF THE INVENTION

In particular, it is known in the art to realize balloon catheters comprising a connector which is mechanically connected to the proximal end of a shaft, in correspondence of a kink.

The connector is usually over-moulded over the kink in order to get a strength connection between the connector and the shaft.

Over-moulding is a well-known process in industrial application but it is not used for PTA balloons.

The main reason is that the shaft has to be very small in order to be inserted through small introducers; moreover the shaft has to resist against high pressure in order to inflate balloons at its distal end.

The problem is increased in shaft of catheters with coaxial or dual-lumen construction. In fact in such devices the shaft having a dual lumen construction is particularly subject to cracks and consequent leakages.

Therefore, it is not known in the art a solution of coaxial or dual-lumen catheter wherein the connector is over-moulded.

SUMMARY OF THE INVENTION

The purpose of the present invention is that of providing a catheter which overcomes the drawbacks mentioned with reference to the prior art; in other words an over-moulded coaxial or dual-lumen catheter which is safe and reliable.

Such aim is reached by catheters and methods as described and claimed herein.

Other embodiments of the catheter according to the invention are described in the subsequent claims.

Further characteristics and advantages of the present invention will be more clearly understood from the description given below with reference to the appended drawings.

BRIEF DESCRIPTION OF THE FIGURES

The elements or parts of elements common to the embodiments described below will be indicated using the same reference numerals.

DETAILED DESCRIPTION

Figure 1:
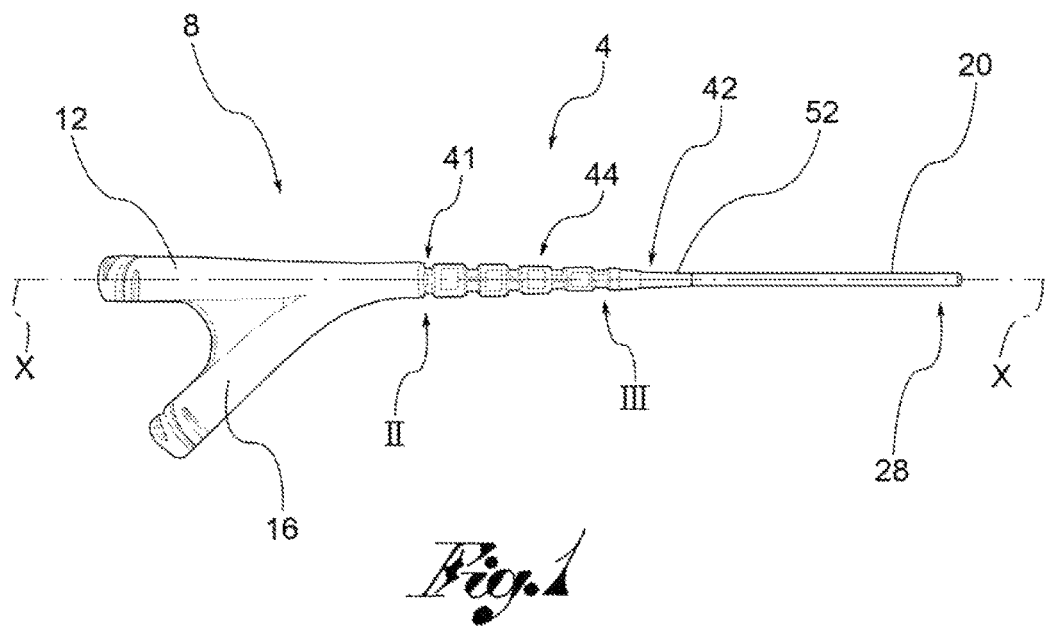
FIG. 1 shows a perspective view of a catheter according to an embodiment of the present invention.
Figure 2:
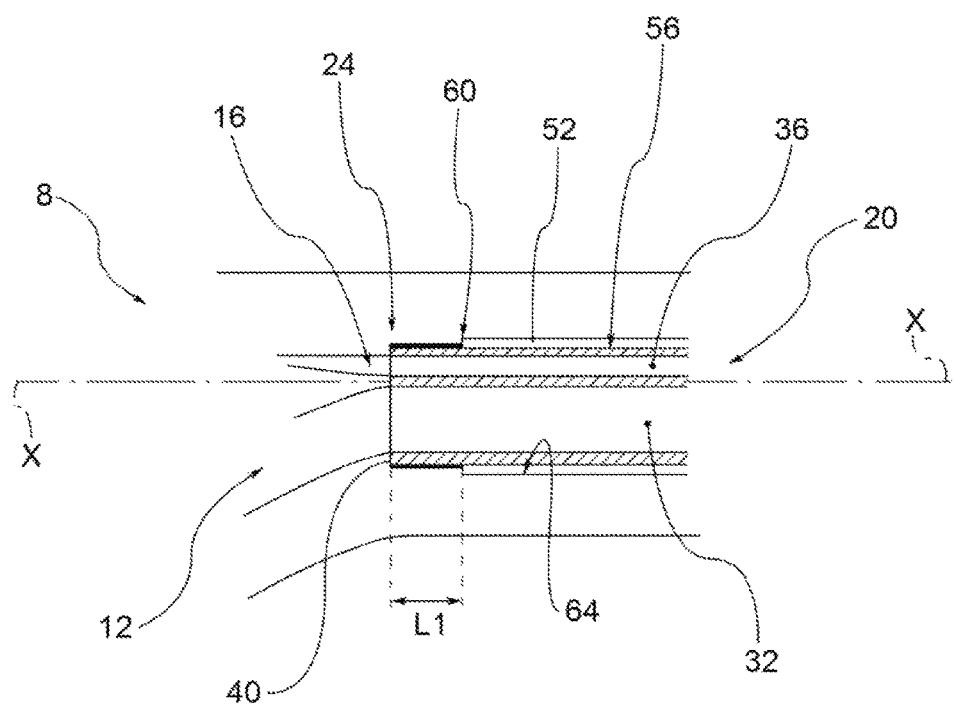
FIG. 2 shows a section view of the particular II of the catheter of FIG. 1.
Figure 3:
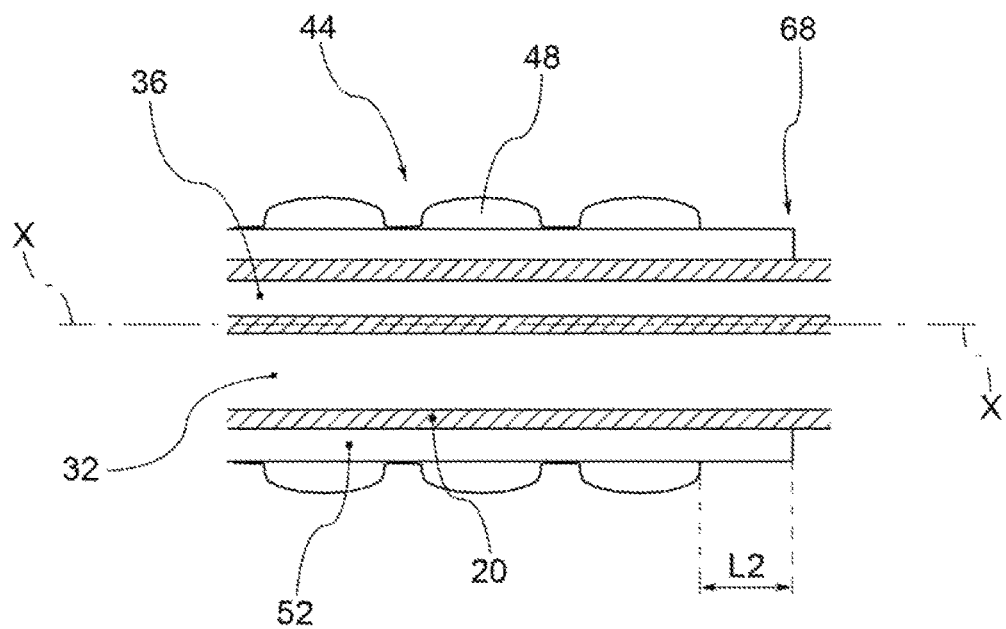
FIG. 3 shows a section view of the particular III of the catheter of FIG. 1.

With reference to the aforementioned figures, reference numeral 4 globally denotes a catheter, in particular, but not exclusively, a catheter for percutaneous transluminal angioplasty (PTA).

The catheter 4 comprises a connector 8 comprising a guide wire channel 12 and an inflation channel 16.

In general, the catheter 4 according to the present invention has a coaxial or dual-lumen construction. Anyway, the catheter may have further lumens for different purposes.

The guide wire channel 12 is useful for housing a guide wire for the guide and the insertion of the catheter 4 in a predetermined vessel. Moreover, the inflation channel 16 is useful in order to send a pressure fluid to the distal end of the shaft. For example the pressure fluid may be air or a liquid. Moreover, the inflation channel may be used as a perfusion channel, for example, of a contrast liquid.

The catheter 4 comprises a shaft 20 extending from a proximal end 24 to a distal end 28 along an axial direction X-X. Moreover, the shaft 20 have a guide wire lumen 32 and an inflation lumen 36.

The shaft 20 is connected, at its proximal end 24, to the connector 8 so that said guide wire lumen 32 and inflation lumen 36 are mechanically and fluidically connected with said guide wire channel 12 and inflation channel 16 of the connector 8, respectively.

According to an embodiment, the proximal end 24 of the shaft 20 is in contact with an axial abutment 40 of the connector 8.

According to an embodiment of the present invention, the shaft 20 and the connector 8 are made up of a polymer material, such as Polyamide, Pebax, Polycarbonate and similar.

Preferably, the shaft 20 and the connector 8 are made up of the same polymer material in order to get a better sealing between them.

The mechanical and fluidical connection between the proximal end 24 of the shaft 20 and the connector 8 is realised in correspondence of a kink portion 44 of the catheter 4, at the proximal end 24 of the shaft 20.

Said kink portion 44 is flexible in order to allow relative bending of the shaft 20 with respect to the connector 8.

According to a possible embodiment of the present invention, the kink portion 44 is made out of the same material as the connector 8; according to another embodiment, the kink portion 44 is made out of a material softer than the connector 8. The kink portion 44 extends from a first kink end 41, axially facing the proximal end of the shaft 20, to a second kink end 42, axially facing the distal end 28 of the shaft 20.

According to an embodiment, the kink portion 44 comprises a plurality of ribs 48 directed both axially and transversally, in a transversal direction Y-Y perpendicular to said axial direction X-X.

Advantageously, the catheter 4 comprises a protective sheath 52 placed around an external wall 56 of the shaft 20, opposite to the guide wire and inflation lumens 32,36.

As better explained hereafter, the protective sheath 52 runs over the shaft 20 and protects the shaft 20 during injection of molten material to over-mould the connector 8.

The protective sheath 52 extends from a first sheath end 60, axially placed at a first distance L1 from the proximal end 24 of the shaft 20 so as to allow a direct contact and a fixing between the external wall 56 of the shaft 20 and an internal wall 64 of the kink portion 44, to a second sheath end 68, axially placed at least in correspondence of the second kink end 42, so as to avoid a direct contact and a fixing between the external wall 56 of the shaft 20 and the internal wall 64 of the kink portion 44.

Preferably, the second sheath end 68 prolongs at a second distance L2 from the second kink end 42 of the kink portion 44.

According to an embodiment of the present invention, the first distance L1 is comprised between 0 and 50 mm.

Preferably, the first distance L1 is comprised between 1 and 20 mm. More preferably, the first distance L1 is comprised between 2 and 10 mm.

According to an embodiment of the present invention, the second distance L2 is comprised between 0 and 100 mm. Preferably the second distance L2 is comprised between 2 and 50 mm. More preferably the second distance L2 is comprised between 2 and 10 mm.

The protective sheath 52 is axially placed around the shaft 20 so as to allow relative movements between them, while bending the catheter 4 in correspondence of the kink portion 44.

Preferably, the protective sheath 52, in correspondence of the second sheath end 68, is tight around the external wall 56 of the shaft 20 so as to avoid any leakage of molten material between the protective sheath 52 and the kink portion 44, during catheter moulding; in this way the shaft 20 is able to axially move relative to the protective sheath 52 during the bending of the kink portion 44.

Figure 4:
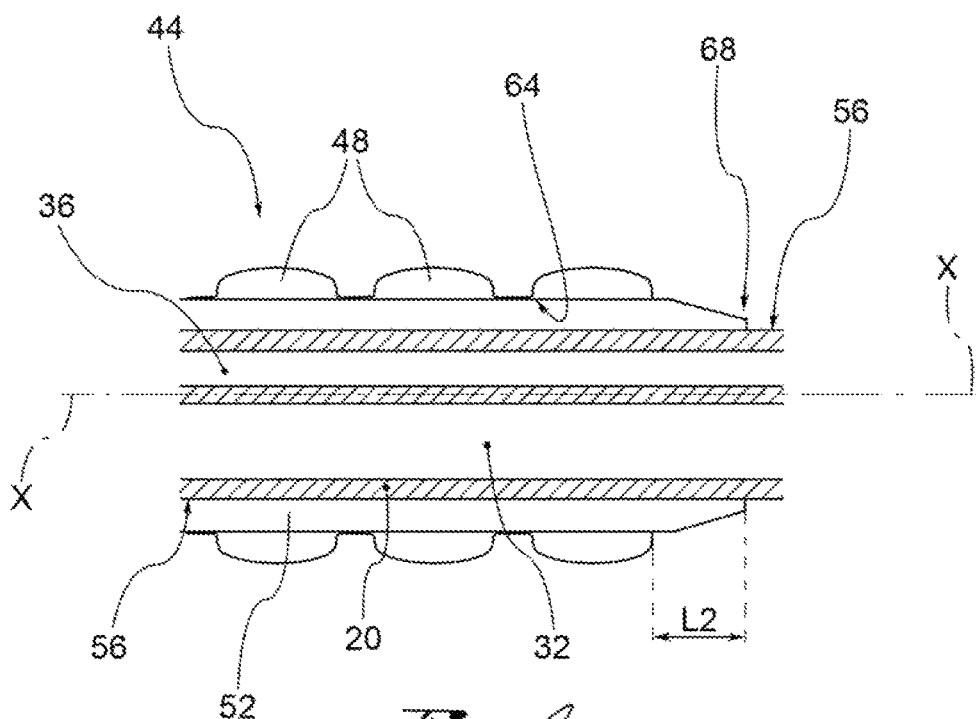
FIG. 4 shows a section view of the particular III of the catheter of FIG. 1, according to another embodiment of the present invention.

According to a possible embodiment of the present invention (FIG. 4) the second sheath end 68 is tapered or chamfered in order to avoid any leakage of molten material between the protective sheath and the kink portion, during catheter moulding. In other words the tapered geometry helps the second sheath end 68 to tight against the external wall 56 of the shaft 20 under the external pressure of the molten injected material.

Hereafter the method of manufacturing a catheter according to the present invention will be described.

In particular the method of producing a catheter 4 according the invention comprises the steps of providing a shaft 20 extending from a proximal end 24 to a distal end 28 along an axial direction X-X, the shaft 20 having a guide wire lumen 32 and an inflation lumen 36.

Then there is the step of providing a protective sheath 52 placed around an external wall 56 of the shaft 20, opposite to the guide wire and inflation lumens 32,36, wherein the protective sheath 52 extends from a first sheath end 60 to a second sheath end 68, and wherein the protective sheath 52 is axially movable with respect to the shaft 20. The first sheath end 60 is axially placed at a first distance L1 from the proximal end 24 of the shaft 20.

Then follows the step of over-moulding, by injection moulding, a connector 8 and a kink portion 44 over the proximal end 24 of the shaft 20, wherein the connector 8 comprises a guide wire channel 12 and an inflation channel 16 fluidically and mechanically connected with the guide wire lumen 32 and the inflation lumen 36 respectively.

The step of over-moulding mechanically connects the external wall 56 of the shaft 20 with the internal wall of the connector 8 along said first distance L1. Moreover, the over-moulding extends till a second kink end 42 of the kink portion 44, which is axially placed before the second sheath end 68 at a second distance L2. In this way it is possible to avoid a direct contact and a fixing between the external wall 56 of the shaft 20 and the internal wall 64 of the kink portion 44, the shaft 20 being able to axially move with respect to the protective sheath 52.

According to a possible embodiment, the method comprises the steps of providing a pre-treatment technique of the proximal end 24 of the shaft 20 in order to improve the sealing between the shaft 20 and the connector 8, such pre-treatment techniques comprising plasma, corona, or chemical treatment or application of primer or glue type materials.

Preferably the shaft 20 and the connector 8 are made up of the same polymer material in order to get a better sealing between them.

As it can be seen from the description, the catheter and relative method of production according to the invention makes it possible to overcome the drawbacks mentioned with reference to the prior art.

In particular, it is possible to make a dual lumen or coaxial catheter with an over-moulding process.

Moreover, the connection of the shaft is safe because there is no redundant link between the shaft and the connector/kink portion. In fact, the shaft is mechanically fixed to the connector at its proximal end but it is free to move with respect to the kink portion thanks to the protective sheath which avoid any redundant connection between the kink portion and the shaft itself.

Moreover the protective sheath protects the shaft during injection moulding, in particular with respect to pressure and heat, but the sheath allows ideal connection of the over-moulding material with the shaft.

In other words, the protective sheath allows a safe and tight connection between the proximal end of the shaft and the connector, by allowing molten material to contact the proximal end of the shaft. At the same time, the protective sheath reduces the heat and pressure transfer to the shaft during injection-moulding. Moreover, the protective sheath, in correspondence of its second sheath end avoids the insertion of molten material between the kink portion and the external wall of the shaft. In this way any redundant connection between the kink portion and the shaft is avoided.

In particular during bending, the shaft is free to axially move with respect to the kink portion thus avoiding excessive mechanical stresses.

A person skilled in the art may make modifications and variations to the catheters and methods described above while remaining within the scope of protection of the invention as described and claimed herein.

The invention claimed is:
1. A catheter comprising
a connector which comprises a guide wire channel and an inflation channel,
a shaft extending from a proximal end to a distal end along an axial direction and having a guide wire lumen and an inflation lumen,
the shaft being connected, at the proximal end, to the connector so that said guide wire lumen and said inflation lumen are mechanically and fluidly connected with said guide wire channel and said inflation channel respectively,
said mechanical and fluid connection being realized at a kink portion of the catheter, at the proximal end of the shaft, said kink portion being flexible to allow bending of the shaft with respect to the connector, wherein the catheter further comprises a protective sheath placed around an external wall of the shaft, opposite to the guide wire lumen and the inflation lumen, the protective sheath extending on a first side from a first sheath end, axially placed at a first distance from the proximal end of the shaft to provide a space between the proximal end of the shaft and the first sheath end so as to allow direct contact between the external wall of the shaft and an internal wall of the kink portion, and on a second side the protection sheath extending to a second sheath end, the second sheath end axially extending at least the same distance as a second kink end of the kink portion, in order to prevent direct contact between the external wall of the shaft and the internal wall of the kink portion.

2. The catheter of claim 1, wherein the second sheath end extends a second distance beyond the second kink end of the kink portion.

3. The catheter of claim 2, wherein the second distance is up to about 100 mm.

4. The catheter of claim 3, wherein the second distance is between about 2 and about 50 mm.

5. The catheter of claim 4, wherein the second distance is between about 2 and about 10 mm.

6. The catheter of claim 1, wherein the first distance is up to about 50 mm.

7. The catheter of claim 6, wherein the first distance is between about 1 and about 20 mm.

8. The catheter claim 7, wherein the first distance is between about 2 and about 10 mm.

9. The catheter of claim 1, wherein the protective sheath is axially placed around the shaft so as to allow relative movements between them, while also allowing bending of the catheter in correspondence to the kink portion.

10. The catheter of claim 1, wherein the protective sheath, in correspondence to the second sheath end, is positioned tightly around the external wall of the shaft so as to avoid any leakage of molten material between the protective sheath and the kink portion, during catheter molding, the shaft being able to axially move relative to the protective sheath during bending of the kink portion.

11. The catheter of claim 1, wherein said second sheath end of the protective sheath is tapered or chamfered to prevent leakage of molten material between the protective sheath and the kink portion, during catheter molding.

12. The catheter of claim 1, wherein the proximal end of the shaft is in contact with an axial abutment of the connector.

13. The catheter of claim 1, wherein the kink portion comprises a plurality of ribs directed both axially and transversally, such that the transversal direction is perpendicular to said axial direction.

14. The catheter of claim 1, wherein the shaft and the connector comprise a polymer material.

15. The catheter of claim 1, wherein the shaft and the connector comprise a same polymer material.

16. The catheter of claim 1, wherein the catheter comprises a coaxial or dual-lumen construction.

17. A method of producing the catheter of claim 1 comprising the steps of:
providing a shaft extending from a proximal end to a distal end along an axial direction, the shaft having a guide wire lumen and an inflation lumen,
providing a protective sheath placed around an external wall of the shaft, opposite to the guide wire lumen and the inflation lumen, the protective sheath extending from a first sheath end to a second sheath end, the protective sheath being axially movable with respect to the shaft,
the first sheath end being axially placed at a first distance from the proximal end of the shaft,
over-moulding, by injection moulding, a connector and a kink portion over the proximal end of the shaft, the connector comprising a guide wire channel and an inflation channel fluidly and mechanically connected with the guide wire lumen and the inflation lumen respectively,
wherein the step of over-moulding mechanically connects the external wall of the shaft with the internal wall of the connector along said first distance,
and wherein the over-moulding extends until a second kink end of the kink portion, said second kink end being axially placed before the second sheath end at a second distance, so as to avoid a direct contact and fixation between the external wall of the shaft and the internal wall of the kink portion, the shaft being able to move axially with respect to the protective sheath.

18. The method of claim 17 comprising the step of providing a pre-treatment technique to the proximal end of the shaft to improve the sealing between the shaft and the connector, wherein such pre-treatment techniques are selected from the group consisting of: plasma, corona, primer application, glue type materials and any combination thereof.

19. The method of claim 17, wherein the shaft and the connector comprise the same polymer material.

\* \* \* \* \*